United States Patent [19]

Smith

[11] 4,199,367
[45] Apr. 22, 1980

[54] ALLOY RAYON

[75] Inventor: Frederick R. Smith, Toms Brook, Va.

[73] Assignee: Avtex Fibers Inc., Valley Forge, Pa.

[21] Appl. No.: 790,129

[22] Filed: Apr. 22, 1977

Related U.S. Application Data

[63] Continuation-in-part of Ser. No. 629,952, Nov. 7, 1975, Pat. No. 4,136,697, and a continuation-in-part of Ser. No. 696,451, Jun. 15, 1976, abandoned, which is a continuation-in-part of Ser. No. 811,793, Jun. 30, 1977, Pat. No. 4,144,079.

[51] Int. Cl.$^2$ ................................................. C08L 1/08
[52] U.S. Cl. .................................... 106/168; 106/169; 264/136; 264/191
[58] Field of Search ........................... 264/188, 191; 260/17.4 CL; 128/156, 284, 285, 290; 106/197 C, 194, 168, 164; 536/98

[56] References Cited

U.S. PATENT DOCUMENTS

| | | | |
|---|---|---|---|
| 2,901,813 | 9/1959 | Schappel | 28/82 |
| 3,005,456 | 10/1961 | Graham | 128/290 R |
| 3,187,747 | 6/1965 | Burgeni et al. | 106/165 |
| 3,318,990 | 5/1967 | Kajitani | 106/164 |
| 3,418,405 | 12/1968 | Kajitani | 264/191 |
| 3,423,167 | 1/1969 | Kuzmak et al. | 264/191 |
| 3,678,031 | 7/1972 | Schoggen | 536/98 |
| 3,719,503 | 3/1973 | Podlas | 99/129 |
| 3,723,413 | 3/1973 | Chatterjee et al. | 128/285 |
| 3,731,686 | 5/1973 | Chatterjee | 128/285 |
| 3,872,196 | 3/1975 | Bridgeford | 264/188 |
| 3,919,385 | 11/1975 | Smith | 264/188 |
| 4,035,195 | 7/1977 | Podlas | 106/194 |
| 4,066,584 | 1/1978 | Allen et al. | 260/17.4 CL |
| 4,104,214 | 8/1978 | Meierhoeter | 260/17.4 CL |
| 4,128,692 | 12/1978 | Reid | 428/378 |

FOREIGN PATENT DOCUMENTS

| | | | |
|---|---|---|---|
| 862130 | 6/1978 | Belgium . | |
| 41-17004 | 9/1965 | Japan | 264/191 |
| 43-7423 | 3/1968 | Japan | 264/191 |

OTHER PUBLICATIONS

"Aquasorb" Data, Bulletin VC-504, Hercules Inc., HER 25018, 4 pages, 7-2-1979.

Primary Examiner—Jay H. Woo
Attorney, Agent, or Firm—Arthur R. Eglington

[57] ABSTRACT

Alloy rayon staple fibers containing about 15 to 35% sodium carboxymethylcellulose based on the weight of cellulose ("b.o.c.") and having high fluid holding capacity at least 5.5 cc per gram (such as in the range of up to about 7 cc/g) measured by the Syngyna test.

4 Claims, No Drawings

ALLOY RAYON

This application is a continuation-in-part of my co-pending applications Ser. No. 629,952 filed Nov. 7, 1975, now U.S. Pat. No. 4,136,697, issued Jan. 30, 1979; and a continuation-in-part of Ser. No. 696,451 filed June 15, 1976, abandoned in favor of continuation-in-part Ser. No. 811,793 filed June 30, 1977, now U.S. Pat. No. 4,144,079, issued Mar. 13, 1979.

This invention relates to alloy rayon staple fibers containing about 15 to 35% sodium carboxymethylcellulose based on the weight of cellulose ("b.o.c.") and having high fluid holding capacity at least 5.5 cc per gram (such as in the range of up to about 7 cc/g) measured by the Syngyna test. In the fiber at least about three fourths of the carboxylic groups of the carboxymethylcellulose are in sodium salt form. The fibers carry a lubricating finish, preferably watersoluble polyoxyethylene sorbitan mono-laurate (e.g. Tween 20) or similar nonionic polyoxyethylene sorbitan monoester of higher fatty acid. The proportion of finish and the proportion of the carboxyl groups which are in sodium salt form are such that when a mass of the fibers is wetted with 2 or more times its dry weight of water and then dried without tension, in air at 25° C. the resulting fibers are substantially non-adherent. The fiber pH (measured on a 1% slurry of these lubricated fibers in deionized water) is in the range of about 5.5 to 8.5 preferably about 6 to 8. Generally the fibers are of about $1\frac{1}{2}$ to 6 denier and the staple fiber length is in the range of about $\frac{3}{4}$ to 5 inches (such as about $1\frac{1}{2}$ inches).

The fibers may be produced by a process which includes the steps of adding carboxymethylcellulose to viscose, spinning the mixture into fiber form into an acid spin bath, washing to remove adhering acid, desulfurizing and treating the fibers with the lubricating finish, the conditions being such that in the course of this treatment at least about three fourths (such as 80%, 90% or more) of the carboxyl groups of the carboxymethylcellulose are converted to the sodium salt form.

Preferably the process is one which yields "chemically crimped" fibers, the spinning conditions being such that the acidic fibers leaving the acid spin-bath are plastic and stretchable (e.g. stretchable by some 60% or more of their length) and are then stretched, as in a hot aqueous bath, to a considerable degree (e.g. some 60% or more such as about 60-70%, after which the stretched acidic fibers are cut to staple length and allowed to relax (e.g. in hot water) and to crimp; then the wet staple fibers are washed, desulfurized and lubricated as described above, in a process including a step of supplying sufficient alkali so as to convert at least three fourths of said carboxyl groups to the sodium form. The fibers may be cut and immediately subjected to the relaxation in hot water at a stage when the regeneration of the cellulose xanthate (to cellulose) has not been fully completed, such as when that degree of regeneration (of the fibers being cut) is less than about 95% but above about 85% such as about 90 to 95%, or after complete regeneration. The relaxation may take place in a conventional bath of hot water (into which chips of parallel fibers, formed by cutting of the tow, fall directly from the cutter); this water may be acidic, neutral or alkaline, e.g. made alkaline with NaOH to a pH of 8 to 11, such as about 10 to 11. A desirable crimp level is at least about 8 distinct crimps per inch (such as about 8 to 20). Discussions of chemical crimping of non-alloy rayon fibers are found, for instance, in Merion et al. U.S. Pat. No. 2,517,694; Textile Research Journal Vol. 23 pp. 137-157 and Man-Made Fibres by Moncrief (6th Edition, 1975, publ. by John Wiley & Sons) pp. 191-193.

The degree and type of fiber lubrication and the degree of conversion of carboxyl groups are such that the wet lubricated fibers have considerable resistance to compaction and tend to separate from each other after they have been squeezed together (to express excess water) under pressure and then released. Thus when the fibers are dried they show little tendency to adhere to neighboring fibers, and the product (particularly after conventional rayon "opening") os made up substantially entirely of individual non-bonded fibers.

The Syngyna test involves the following procedure: the fibers are carded into web form and then separated into 2.5 gram portions each about 6 inches long. Each such web portion is then individually rolled in the direction of its width to provide a six inch roll and a string is looped about the center thereof. Each such roll is then folded on itself at the string loop and drawn into a $\frac{1}{2}$ inch tube within which it is compressed by a clamp and plunger, thus forming a tampon. The resulting tampons are removed, allowed to stand for a period of about 30 minutes (during which the tampons recover to a bulk density of about 0.4 cc/g) and are then evaluated for their capacity to hold water by the Syngyna Method, as described by G. W. Rapp in a June 1958 publication of the Department of Research, Loyola University, Chicago, Illinois.

The alloy fibers of the present invention are adapted for use in a variety of articles, such as sanitary menstrual napkins and vaginal tampons, in which high fluid retention is an essential characteristic. In the manufacture of such articles, the alloy fibers may be used in the same manner and with the same equipment as employed with conventional rayon fibers are they may be blended with other fibers which may or may not enhance the absorbent properties of the resulting articles. Fibers with which the alloy fibers of the present invention may be blended include, for example, rayon, cotton, chemically modified rayon or cotton, cellulose acetate, nylon, polyester, acrylic, polyolefin, etc. Typically a tampon is an elongated cylindrical mass of compressed fibers, supplied within a tube which serves as an applicator; see U.S. Pat. Nos. 2,024,218; 2,587,717; 3,005;456; 3,051,177.

The spin bath is an acid bath containing sulfuric acid and sodium sulfate and usually, zinc sulfate. Other coagulation modifiers, as desired, may be present. It is preferred that the $H_2SO_4$ concentration be on the relatively low side, such as 6.0 or 6.8% or (with appropriate other conditions) in a range of about 5.5-8%. During the spinning of the viscose into the acid bath, hydrogen ions diffuse into the stream of viscose emerging from each spinneret hole. The reaction of the acid with caustic soda in the viscose produces sodium sulfate and water; the acid also decomposes xanthate groups. The presence of sodium sulfate in the spin bath acts to induce coagulation of the viscose streams owing to dehydration from the interiors of the streams. Zinc ions in the spin bath act, at least at the surfaces of the streams, to convert sodium cellulose xanthate of the viscose to zinc cellulose xanthate which is decomposed more slowly by the acid and thereby keeps the fiber in more stretchable and orientable condition. Typically the temperature of the acid bath is in the range of about 45 to 65° C. (such as about 50°-55° C.) and the fiber, after passing through the acid bath, is subjected to a bath of water (or dilute acid) first at a high temperature such as about 80° C. to the boiling point, e.g. about 85-95° C., and/or to steam and then to water at a moderate temperature such as about 40° to 50° C. In the high temperature aqueous treatment the fibers are subjected to stretching. While for most uses the fibers need not have high strength properties, the alloy fibers have been found to retain to a very large extent the physical properties of non-alloy rayon. Typically, the alloy fibers of this invention are not brittle and may be processed in about the same ways as ordinary rayon.

While the polyoxyethylene sorbitan monoester of higher fatty acid (such as Tween 20) is a preferred finish, it is within the broader scope of the invention to employ other lubricating finishes, preferably applied in aqueous solution or dispersion, such as soaps; sulfonated oils; ethoxylated fatty acids; ethoxylated fatty ester of polyhydric alcohols; fatty acid esters combined with emulsifying agents (including Tweens); or mixtures of various lubricating finishes. Generally the amount of lubricating finish deposited on the fiber will be well below 1%, and usually more than 0.05, such as in the range of about 0.1 to 0.5% or 0.1 to 0.3%. Preferably it is not such as to give the fibers an oily feel.

The carboxymethyl cellulose may be the sole high polymeric additive in the viscose or it may be used together with other water-soluble (including aqueous alkalisoluble) high polymers. Preferably these are anionic polymers such as polymeric acids or salts (e.g. alkali metal salts) thereof, e.g. salts of other carboxyalkyl celluloses (such as sodium carboxyethyl cellulose), salts of polyacrylic acids, (including polyacrylic acid or polymethacrylic acid homo-polymer, or copolymers of acrylic and/or methacrylic acid with one or more other monomers such as acrylamide or alkyl acrylates, e.g. ethyl acrylate), salts of copolymers of maleic or itaconic acid with other monomers such as methyl vinyl ether, or naturally occurring polycarboxylic polymers, such as algin. These materials are preferably dissolved in aqueous medium before addition to the viscose, the solution being preferably alkaline, e.g., they may be made with an amount of alkali, such as NaOH, stoichiometrically equivalent to the amount of acidic (e.g. carboxyl) groups of the polymer or with an excess of alkali. Less desirably, these materials may be added in acid form (again preferably as aqueous solutions) and be converted to salt form by the action of the alkali present in the viscose. When another anionic polymer is present, it is within th broader scope of the invention to reduce the proportion of the sodium carboxymethylcelluose; for instance one may use, say, 7% sodium polyacrylate and 8% sodium carboxymethylcelluose b.o.c. or 10% each of these. Other water-soluble high polymers include polyvinyl pyrollidone or substantially non-ionic polymers such as starch (which may be added as, say as alkaline solution containing some 2-5% of NaOH) or polyvinyl alcohol.

The following Examples illustrate the invention further.

EXAMPLE I

Using conventional rayon spinning equipment an aqueous alkaline solution of sodium carboxymethylcellulose of 7M grade (Hercules, having an average degree of substitution of 0.7 carboxymethyl units per anhydroglucose unit of the cellulose and having a molecular weight such that the viscosity of a 2% solution thereof in water is about 300 cps) is injected by a metering pump into a viscose stream during its passage through a blender and the blend is thereafter extruded. During this the blend is subjected to high mechanical shearing. The viscose composition is 9.0% cellulose, 6.0% sodium hydroxide and 31% (based upon the weight of the cellulose) carbon disulfide. The viscose ball fall is 60 and its common salt test is 7. In making the alkaline CMC feed solution the sodium carboxymethylcellulose (CMC) is added to a 6% aqueous solution of NaOH to form a uniform solution having a ball fall viscosity of 120 seconds (which is a viscosity of about 13,000 cps). The amount of CMC is such as to provide 20% thereof based on the weight of cellulose.

The mixture of viscose and sodium carboxymethylcellulose is extruded through a spinneret (having 980 circular holes, each 0.0035 inch in diameter) into an aqueous spinning bath consisting of 6.0% by weight of sulfuric acid, 21% by weight of sodium sulfate, and 1.0% by weight of zinc sulfate at 55° C.

The tow formed in the spin bath is passed around a driven roll and then pulled (by a second driven roll) through a hot aqueous stretch bath (e.g. containing about 3 to 5% $H_2SO_4$ and at about 85° C. or higher). The exit speed (i.e., the speed at the surface of the second driven roll) is 40 meters/minute, and the speed ratio of the first and second driven rolls in such that the tow is stretched about 60 to 70% in the stretch bath.

The length of travel of the tow in the spin bath is about 0.4 meter and in the stretch bath about 2 meters. After leaving the second driven roll, the tow drops into a cutter and the resulting cut fibers drop into flowing hot water (about 85° to 90° C.) where relaxation (and crimping) occurs. This 3 d.p.f. staple fibers are taken up as a blanket, washed with hot water for 8 minutes at 90° C.; treated for 8 minutes in a 0.5% NaOH solution at 40° C. (or equivalent solution of sodium carbonate or sodium sulfide) to neutralize the adhering acid; washed again in water for 4 minutes at 40° C.; bleached and desulfurized in an aqueous solution of sodium hypochlorite containing about 0.2% available chlorine and about 0.2% NaOH at 40° C. for 3 minutes; washed with soft water for 8 minutes at 40° C. (if the pH of the final dried product indicates the presence of free alkali [e.g. NaOH] in the fiber, the process may be modified to include addition of dilute $H_2SO_4$ to the wash water in amount sufficient to neutralize the free alkali). To the fibers there is then applied an aqueous solution of 0.3% Tween 20, after which the fibers are squeezed to remove adhering water and then dried (e.g. at about 90° C.) without tension. In squeezing to remove water, the blanket (about 2 to 4 inches thick) of the staple fibers is passed between stainless steel pressure rolls, the blanket being in the nip of this pair of rolls for less than 2 seconds and the pressure being such that the average water content of the blanket is reduced thereby to less than about 100% (e.g. about 80%). The blanket is then passed over a beater having a rotating spiked roll which tears it into chunks (e.g. of 1 to 2 inch diameter, or more) of fiber before drying, e.g. in hot air at 70° or 90° C.

EXAMPLE II

A viscose solution is prepared to contain 9% cellulose, 6% NaOH and 31% $CS_2$ based on cellulose content and aged, for spinning, to a ball-fall viscosity of 44 seconds and salt index of 5.8.

A solution of sodium carboxymethyl cellulose (CMC7L, Hercules, Inc.) is prepared to contain 9% CMC dissolved in 6% NaOH.

The CMC solution is mixed with the viscose solution, just before spinning, by use of a metering pump. The mixed solutions are pumped through a 980 hole jet at a rate to make 3 denier filaments, the jet being immersed in a spin bath containing 6% $H_2SO_4$, 0.78% $ZnSO_4$ and 21.3% $Na_2SO_4$ at 54° C. After travelling 20 inches through the spin bath the yarn bundle is passed around a guide, a godet wheel, through a cascade trough and around a pair of wash drums. The cascade trough contains an aqueous 2 to 3% $H_2SO_4$ solution at 90° C. The wash drums have a perpheral speed sufficiently higher than that of the godet wheel that the yarn is stretched about 76%. The yarn is washed with water until free of spin-bath chemicals.

Portions of the yarn are cut about 1½ inches long, treated with sufficient ½% NaOH to convert all the carboxyl groups to sodium form, washed with water and immersed in 0.3% Span 20 solution. Excess solutions is removed by centrifuging. The samples are dried and evaluated for fluid holding capacity using the Syngyna test.

The same process is carried out with a control and with different proportions of CMC injected into the viscose solution, with the following results in terms of fluid holding capacity:

| Sample | % CMC b.o.c.* | Fluid held cc/q |
|--------|---------------|-----------------|
| A | 0 | 4.32 |
| B | 10 | 4.94 |
| C | 20 | 5.86 |
| D | 30 | 6.63 |

*% Sodium carboxymethylcellulose, based on cellulose; calculated by dividing the weight of the sodium carboxymethylcellulose added to the viscose solution by the weight of the cellulose in that viscose solution (prior to the addition of CMC).

The invention has been illustrated more particularly in connection with sodium carboxymethylcellulose having a degree of substitution in the range of about 0.6 to 1 such as Hercules 7M (having about 0.65–0.85 carboxymethyl groups per anhydroglucose unit and a degree of polymerization ["D.P."] of about 500) or Hercules 7L (also having about 0.65–0.85 carboxymethyl groups per anhydroglucose unit but whose D.P. is about 300). It is also within the broader scope of the invention to employ CMC of higher degree of substitution such as about 0.9 or even 1.2 or 1.4 and CMC of higher or lower molecular weight (e.g. a D.P. of about 1000 or about 200 or even 100).

It is understood that the foregoing detailed description is given merely by way of illustrated and that variations may be made therein without departing from the spirit of the invention.

I claim:

1. Alloy rayon staple fibers containing about 15 to 35% sodium carboxymethylcellulose b.o.c., at least about three fourths of the carboxyl groups of said sodium carboxymethylcellulose being in sodium salt form, said fibers having a denier of about 1½ to 6, said fibers carrying a lubricating finish in amount of less than 1% and said fibers having a fluid holding capacity of at least about 5.5 cc per gram as measured by the Syngyna test.

2. Alloy rayon staple fibers as in claim 1 in which said lubricating finish is water-soluble.

3. Alloy rayon staple fibers as in claim 2 in which said lubricating finish is a nonionic polyoxyethylene sorbitan monoester of a higher fatty acid.

4. Alloy rayon staple fibers as in claim 1 produced by incorporating sodium carboxymethylcellulose in said proportion into a viscose solution, spinning the mixture into fiber form into an acidic spin bath containing sulfuric acid and sodium sulfate, to form a stretchable fiber, stretching said fiber in a hot aqueous medium, cutting said stretched fibers into staple form and relaxing said cut fibers in a hot water bath, washing said cut fibers and applying said finish in aqueous medium, the acidity of said stretched fibers being neutralized to such an extent during said process that at least about three fourths of said carboxyl groups are in sodium salt form.

* * * * *

UNITED STATES PATENT AND TRADEMARK OFFICE
CERTIFICATE OF CORRECTION

PATENT NO. : 4,199,367
DATED : April 22, 1980
INVENTOR(S) : Frederick R. Smith

It is certified that error appears in the above-identified patent and that said Letters Patent are hereby corrected as shown below:

Column 2, line 14: "os" should read "is"

Column 5, line 1 : "carboxymethyl cellulose" should read "carboxymethylcellulose"

Column 5, line 21 & 22: should read in part "Excess solution is removed by centrifuging."

Column 6, line 21: should read in part "finish in an amount less than 1%."

Signed and Sealed this

Twenty-eighth Day of October 1980

[SEAL]

Attest:

Attesting Officer

SIDNEY A. DIAMOND

Commissioner of Patents and Trademarks